United States Patent [19]

Hojaiban et al.

[11] Patent Number: 5,879,293

[45] Date of Patent: Mar. 9, 1999

[54] NON-INVASIVE UTERINE ACTIVITY SENSOR

[75] Inventors: George Hojaiban, Meriden; Donald Malinouskas, Monroe, both of Conn.

[73] Assignee: SpaceLabs Medical, Inc., Redmond, Wash.

[21] Appl. No.: 666,886

[22] Filed: Jun. 19, 1996

Related U.S. Application Data

[60] Provisional application No. 60/002,674 Jun. 20, 1995.

[51] Int. Cl.$^6$ ...................................................... A61B 5/00
[52] U.S. Cl. ........................... 600/310; 600/473; 600/476; 600/591
[58] Field of Search .................................... 128/633, 664, 128/665, 666, 687, 688, 689, 690, 774, 775, 778; 600/310, 473, 476, 500, 503, 587, 588, 591, 571

[56] References Cited

U.S. PATENT DOCUMENTS

| | | | |
|---|---|---|---|
| 4,281,645 | 8/1981 | Jobsis | ........................................ 128/633 |
| 4,807,630 | 2/1989 | Malinouskas . | |
| 5,277,181 | 1/1994 | Mendelson et al. | ...................... 128/633 |
| 5,299,570 | 4/1994 | Hatschek | ................................. 128/633 |
| 5,406,961 | 4/1995 | Artal . | |
| 5,450,857 | 9/1995 | Garfield et al. . | |

FOREIGN PATENT DOCUMENTS 144575    3/1959    U.S.S.R. .

OTHER PUBLICATIONS

Haumschild, D. J., "Microvascular blood flow measurement by laser Doppler flowmetry," TSI Application Note, TSI Incorporated, St. Paul, Minnesota, 1986.

Nellcor Incorporated's Reference Note entitled "Technical Issues of Noninvasive Fetal Osygen Saturation Moniroting Using the *Nellcor®* N–400," Nellcor Incorporated, Pleasanton, California, 1994.

Reynolds, S. R. M., *Physiology of the Uterus*, Paul B. Hoeber, Inc., New York, 1949, pp. 42–53.

Translation of Pat. No. 144575 (SU, 1959), Item #4 above.

*Primary Examiner*—Marvin M. Lateef
*Assistant Examiner*—Eleni Mantis Mercader
*Attorney, Agent, or Firm*—Seed and Berry LLP

[57] ABSTRACT

Uterine activity is sensed by passing light through the patient's abdominal wall and detecting the light reflected from abdominal tissues. The intensity of the reflected light varies with the state of contraction of the patient's uterus. The use of light for monitoring uterine activity avoids the problems of size, fixation, and measurement accuracy exhibited by the conventional tocodynamometer technique.

11 Claims, 8 Drawing Sheets

NON-INVASIVE UTERINE ACTIVITY SENSOR

CROSS REFERENCE TO RELATED PROVISIONAL APPLICATION

This application claims the benefit under 35 USC § 119(e) of U.S. Provisional Application No. 60/002,674, filed Jun. 20, 1995.

BACKGROUND OF THE INVENTION

1. Field of the Invention

This invention relates to the non-invasive sensing, detecting, and/or monitoring of uterine activity, including uterine contractions.

2. Description of the Prior Art

Tocodynamometers have been and are being used to non-invasively monitor uterine contractions. Such devices mechanically sense the hardness of the abdominal wall. These devices suffer from a number of problems, the primary one of which is that they provide relative data which in many cases does not reflect the actual intensity of uterine contractions. Also, the devices are large, require belts for attachment to the patient, and are sensitive to movement of the device relative to the patient's abdomen.

SUMMARY OF THE INVENTION

In view of the foregoing it is an object of the present invention to provide improved methods and apparatus for sensing uterine activity.

To achieve this and other goals, the invention provides an optical method for sensing uterine activity and apparatus for practicing that method. In accordance with the invention, light of one or more wavelengths is applied to the patient's abdomen from a suitable source or sources and light modulated by the tissues and blood of the patient (referred to hereinafter collectively as the "tissues") is detected by one or more sensors. As described below, it has been found that uterine activity modulates the applied light such that time variations in the detected light correspond to uterine activity and thus can serve to monitor such activity.

In certain preferred embodiments of the invention, light of a single wavelength is used. The wavelength can be selected from any part of the spectrum. Preferably, the wavelength is in a range where the absorptions of at least some of the hemoglobin fractions of the blood are similar. In particular, a wavelength in the range where the absorptions of the major hemoglobin fractions are similar is preferred, e.g., a wavelength in the range where the absorptions of oxyhemoglobin and deoxyhemoglobin are similar. For example, a light source having a wavelength of about 500–600 nm or about 800 nm can be used.

In other preferred embodiments of the invention, light of two wavelengths is used, and the output signal for monitoring uterine activity is based on a comparison between the detected light at the two wavelengths. The two wavelengths can be selected from any part of the spectrum. As in the one wavelength embodiments, one or both of the two wavelengths can be from a region of the spectrum where the absorptions of the various hemoglobin fractions of the blood, in particular, the oxyhemoglobin and deoxyhemoglobin fractions, are similar.

The one wavelength embodiments allow for detection of uterine activity. The two wavelength embodiments can be used for the same purpose and can improve the reliability of the system by eliminating unwanted artifacts such as baseline drift. More than two wavelengths can be used if desired to even further refine the analysis.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

Figure 1:
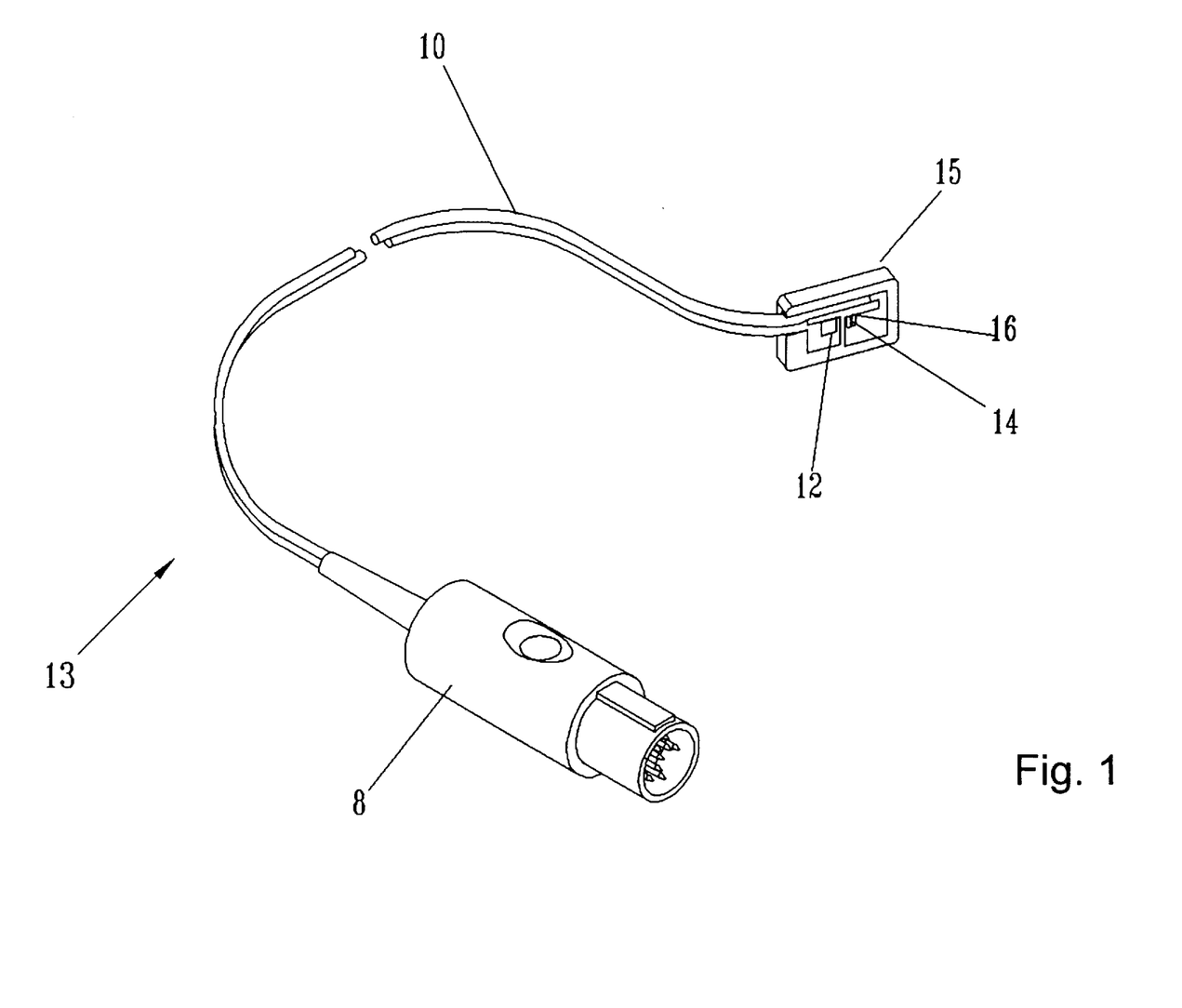
FIG. 1 is a schematic drawing of a uterine activity sensor constructed in accordance with the present invention.

FIG. 1 shows a uterine activity sensor 13 constructed in accordance with the invention. Sensor 13 includes: head 15, which carries light detector 12 and light sources 14 and 16; connecting cable 10; and connector 8 for attachment to a suitable monitor (not shown). Light sources 14 and 16 of this figure are designed to operate at different wavelengths.

Figure 2A:
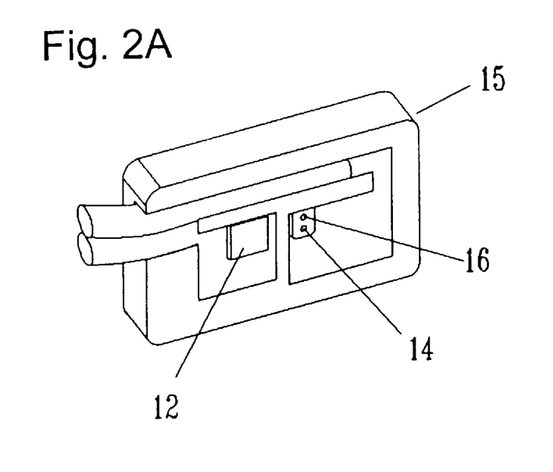
FIG. 2A is an expanded view of the head portion of the sensor of FIG. 1.
Figure 2B:
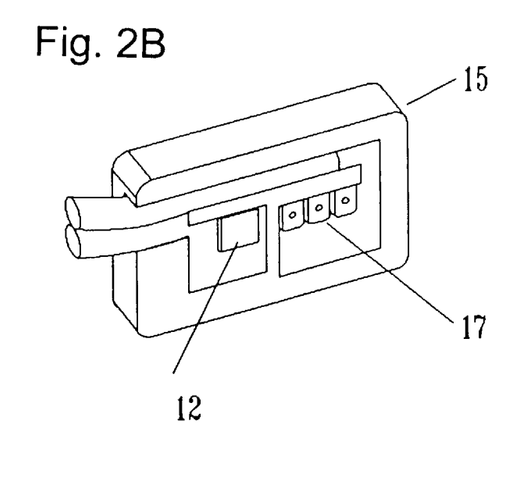
FIGS. 2B and 2C show alternate constructions for the head portion of the sensor of FIG. 1.
Figure 2C:
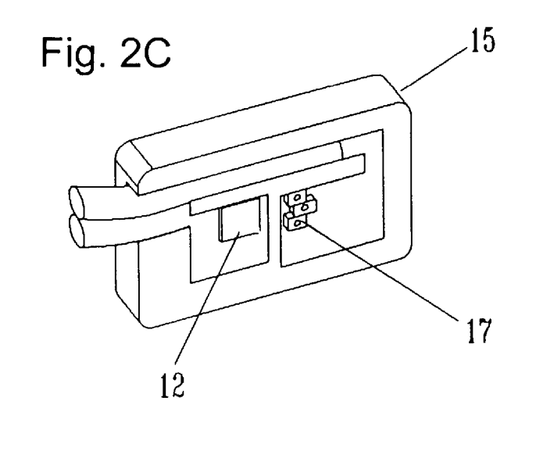

FIG. 2A shows an expanded view of head 15 where light sources 14 and 16 can be more readily seen. FIGS. 2B and 2C show alternate constructions employing three light sources 17, each designed to operate at the same wavelength. In FIG. 2B, the three light sources are arranged in a linear array, while in FIG. 2C, they are in an arcuate array. The optimum spacing between the light sources and detector 12 will depend upon the light intensity generated by the sources and the amount of absorption of that light by the patient's tissue, such absorption being a function of the wavelength used, with shorter wavelengths generally undergoing greater absorption than longer wavelengths. More or less light sources can, of course, be used in both the single and multiple wavelength embodiments of the invention. Also, different light source arrangements besides those shown in FIGS. 1 and 2 can be used if desired.

In the case of the single wavelength embodiments of the invention, the wavelength of the light source is preferably chosen to be in a range where the absorptions of at least some of the hemoglobin fractions of the blood are similar. In particular, a wavelength in the range where the absorptions of the major hemoglobin fractions are similar is preferred. For most patients, the major hemoglobin fractions are oxyhemoglobin and deoxyhemoglobin. Accordingly, a wavelength in the range where the absorptions of these two fractions are similar is especially preferred.

Figure 3:
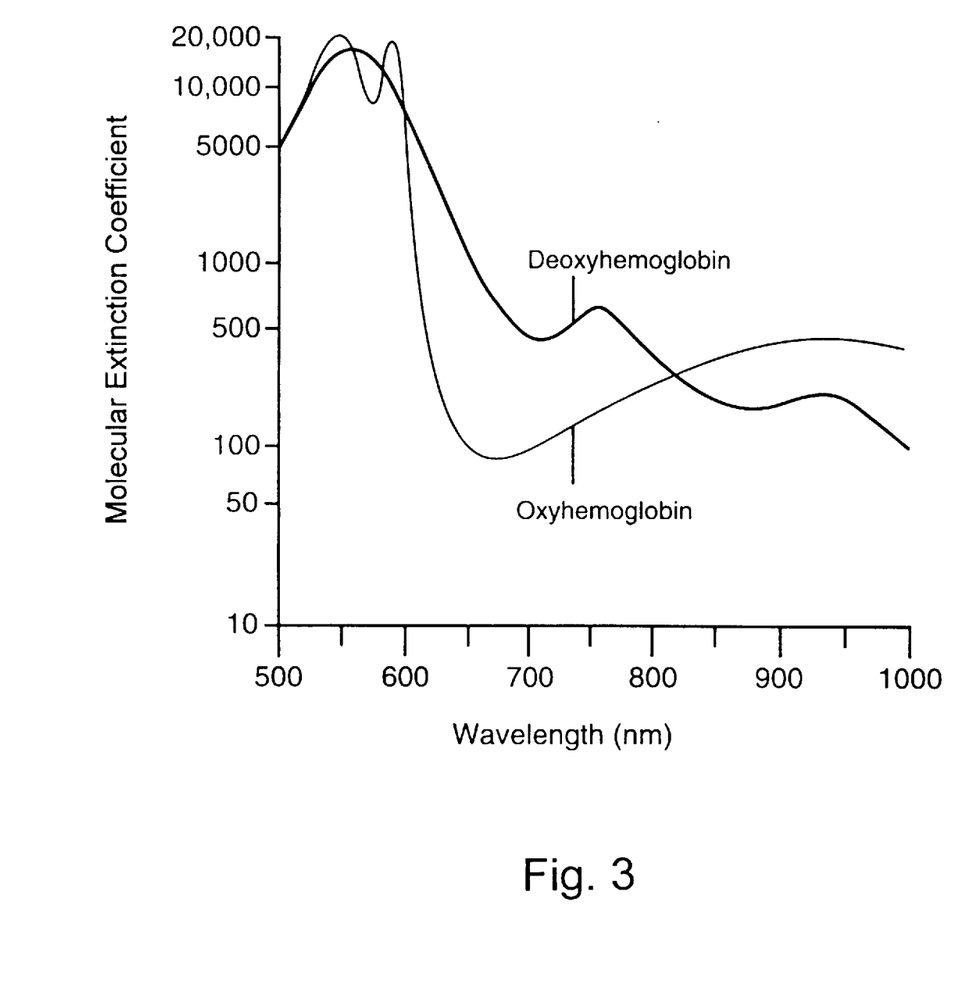
FIG. 3 is a plot of molecular extinction coefficient versus wavelength for oxyhemoglobin and deoxyhemoglobin.

FIG. 3 is a graph of the absorption spectra (more specifically, the molecular extinction coefficients) of oxyhemoglobin and deoxyhemoglobin. As can be seen in this figure, the absorptions of these two fractions are similar at around 500–600 nm and around 800 nm. In the 600 nm range, the absorptions of oxyhemoglobin, deoxyhemoglobin, carboxhemoglobin, and cyanhemoglobin are all similar, making this wavelength range especially preferred.

To the extent available, a light source which has a wavelength where the oxyhemoglobin and deoxyhemoglobin absorptions are identical is preferred. However, commercial light sources are not generally available at such wavelengths and thus a light source is used where the absorptions are similar, although not identical. The purpose of using a wavelength where the absorptions are similar is to reduce the effects of the level of oxygen saturation of the patient's blood on the monitoring/detecting of uterine activity. Accordingly, in this context, a wavelength for which absorptions are "similar" is one which achieves such a minimization. In terms of the 500–600 nm and 800 nm values referred to above, wavelengths in the 475–625 nm and the 775–825 nm range generally meet this criterion, although the absorption spectra for the hemoglobin fractions of interest should be examined to determine whether the criterion is reasonably satisfied for any particular light source, taking into account the spectral spread of the source. The invention, of course, is not restricted to the above ranges of values and can be practiced at any wavelength from any part of the spectrum if desired.

Similar considerations apply to the multiple wavelength embodiments. Thus, at least one of the wavelengths used in such an embodiment preferably falls in a range where the effects of the level of oxygen saturation of the patient's blood is minimized. The various factors discussed above for the single wavelength embodiments apply in the selection of such a wavelength. If desired, all of the wavelengths used in a multiple wavelength embodiment can be chosen to minimize the effects of the level of oxygen saturation.

Alternatively, oxygen saturation effects can be minimized by the selection of a pair or a set of wavelengths which balance the effect. For example, two wavelengths can be used wherein absorption increases with increasing oxygen saturation for one of the wavelengths and decreases with oxygen saturation at the other wavelength, the increase and decrease being approximately the same. Addition of signals for the two wavelengths will then cancel out the effects of oxygen saturation at least to some extent. Similarly, two wavelengths which respond in the same direction to oxygen saturation can be used, with the signals being subtracted in this case.

Light sources 14, 16, and 17 can be light emitting diodes (LEDs) or broadband sources in combination with suitable filters. Other light sources can be used if desired. Light detector 12 can be a broadband photodiode. Again, other types of detectors can be used if desired.

As is well known in the art, light sources, including LED light sources and filtered broadband sources, do not generate a single wavelength. Such sources, however, do have a wavelength or narrow range of wavelengths of maximum intensity. References herein to a "single wavelength," "two wavelengths," and "multiple wavelengths" are to such a wavelength or narrow range of wavelengths of maximum intensity produced by practical light sources.

Light sources 14 and 16 can operate at, for example, 640 nm (red) and 940 nm (IR). However, it has been found that for some patients, tracings at 640 nm appear to be responsive to both uterine contractions and to changes in the level of oxygen saturation of the blood passing through the patient's abdomen. This complicates the analysis by adding an additional variable. Similar effects can occur at 940 nm, although generally to a lesser extent. Accordingly, for general use and for the reasons discussed above, preferred wavelengths for a two wavelength system are selected from the group consisting of about 550 nm (e.g., 550±25 nm), about 600 nm (e.g., 600±25 nm), or about 800 nm (e.g., 800±25 nm). Similar wavelengths can be used for a single wavelength embodiment. In practice, the 550 nm and 600 nm wavelength ranges are somewhat easier to implement than the 800 nm range since LEDs are readily obtainable at these shorter wavelengths, e.g., LEDs operating at 570 nm or 605 nm. For either the multiple or single wavelength embodiments, other wavelengths besides those specifically discussed herein can, of course, be used if desired.

As can be seen in FIG. 3, as the wavelength decreases the absorption level increases. This has both advantages and disadvantages. With regard to advantages, the shorter wavelengths are more responsive to changes in the amount of blood in the abdominal muscles and thus can be a better detector of uterine activity. With regard to disadvantages, the shorter wavelengths undergo greater absorption and thus generally have reduced penetration into the abdominal wall and generally produce smaller signals. These disadvantages can be addressed by using multiple light sources such as those shown in FIGS. 2B and 2C. It should be noted that multiple light sources can be used for both the single wavelength and multiple wavelength embodiments.

Cable 10 of FIG. 1 contains multiple conductors for supplying drive current to the light sources and for transmitting the detector's output signal to the monitor.

The monitor can have various constructions known in the art for driving light sources and processing the output of light detectors. U.S. Pat. No. 4,807,630 (the "'630 patent") shows a system for processing light of two wavelengths in the context of a pulse oximeter. This system is insensitive to ambient light and 60 hertz interference and is suitable for use with the present invention. Other monitor configurations, of course, can be used in the practice of the present invention if desired.

Figure 4:
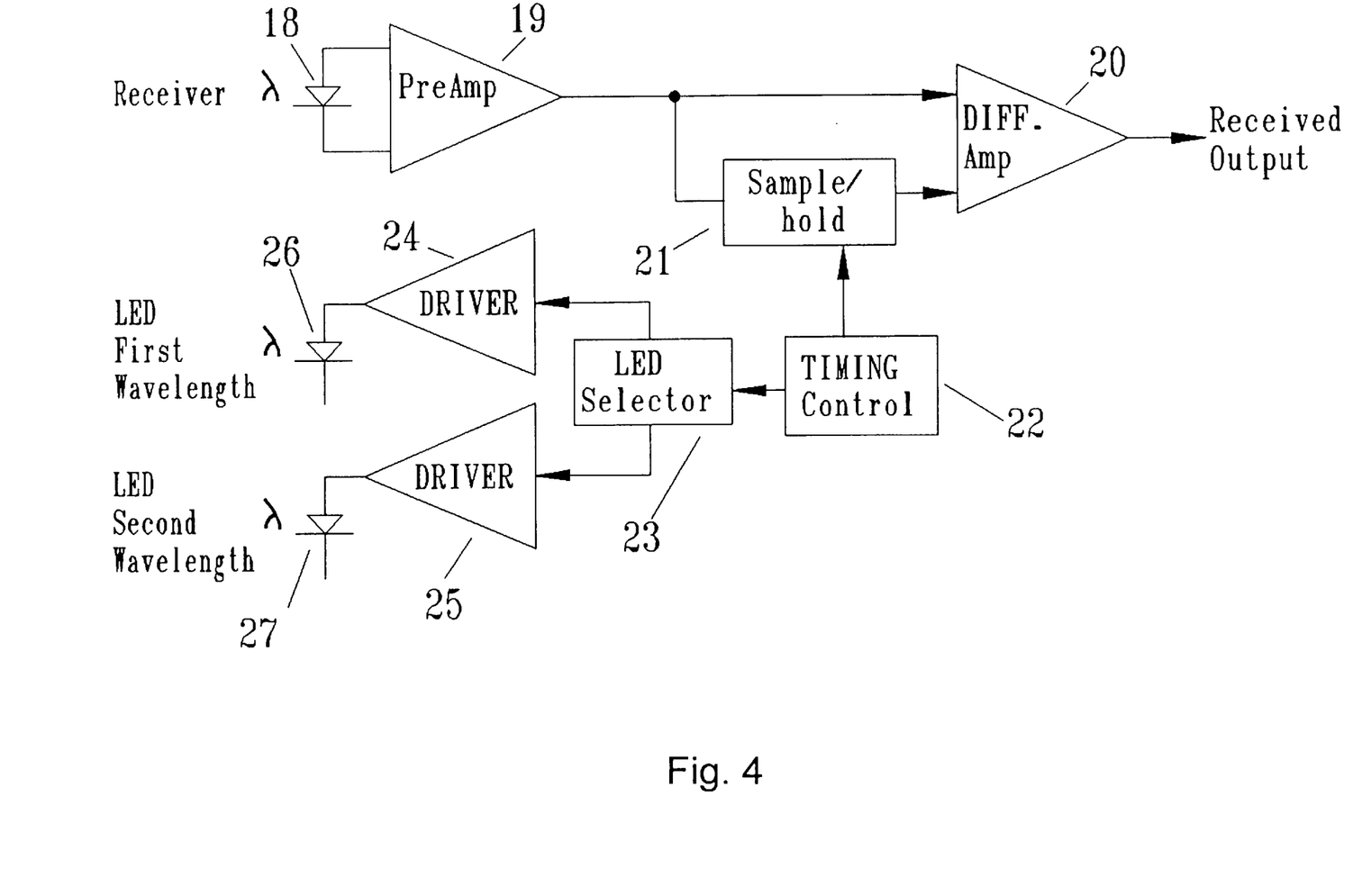
FIG. 4 is a circuit diagram for use with the sensor of FIG. 1.
Figure 5:
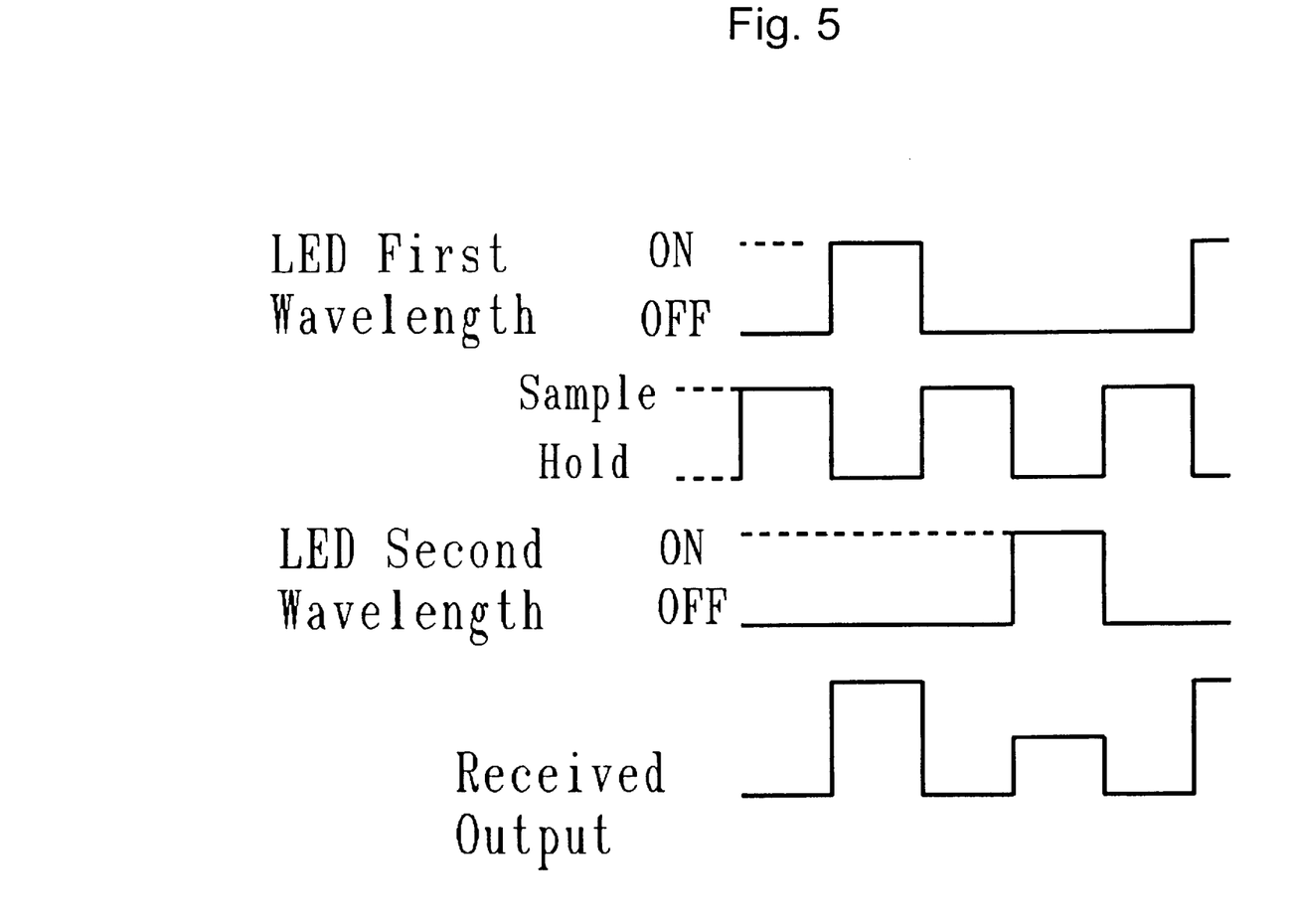
FIG. 5 is a timing diagram for the circuit of FIG. 4.

For example, FIGS. 4 and 5 show a circuit and timing diagram which can be used in the practice of the invention. In comparison to the circuit of the '630 patent, the circuit and timing diagram of these figures allows for high intensity pulsing of the light producing LEDs. LEDs can generally withstand short current pulses substantially above their continuous current rating, e.g., 10 times their average current rating. In response to such current pulses, LEDs produce high intensity light bursts. Such high intensity bursts of light achieve better penetration of the patient's tissues and a stronger signal at detector 12. The use of current pulses, as opposed to a continuous drive signal, also has the advantage of minimizing heating of head 15 of sensor 13 which some patients may find uncomfortable.

With reference to FIG. 4, timing control circuit 22 generates a timing signal which is fed to LED selector 23 and to sample/hold circuit 21. LED selector 23 determines which of drivers 24 and 25 are active. These drivers are connected to LEDs 26 and 27, which, for example, can generate light at wavelengths of about 570 nm and about 605 nm.

Receiver 18 comprises a broadband photodiode which is connected to preamplifier 19. The signal from the preamplifier is fed to differential amplifier 20 where it is combined with a signal from sample/hold circuit 21 (see discussion below). The output of differential amplifier 20 provides alternating received signals for the first and second wavelengths in accordance with the timing chart of FIG. 5.

As shown in FIG. 5, the overall timing of the system comprises four sequential timing periods (see the sample/hold trace of this figure). During the first timing period, both LEDs 26 and 27 are turned off and the preamplifier output is fed to the sample/hold circuit to measure the ambient background noise level of the system, including any 60 hertz noise present in the vicinity of the patient. During the second timing period, LED 26 is turned on and the output of the preamplifier and the signal from the sample/hold circuit for the previous time period are fed to differential amplifier 20. The amplifier subtracts the two signals, thus removing the ambient background noise from the received light signal for LED 26.

During the third timing period, both LEDs are again turned off and the ambient background noise is again sampled and held in sample/hold circuit 21. Finally, during the fourth timing period, the signal for LED 27 is obtained with the ambient background noise again be subtracted through the joint operation of sample/hold circuit 21 and differential amplifier 20.

The various circuits of FIG. 4 can be constructed using conventional electronic components well known in the art. The sample/hold switch incorporated within the circuit should have low gate charge injection so that spikes are not produced at its output at the beginning and the end of the timing pulses. Similarly, amplifiers 19 and 20 should be sufficiently fast to accurately follow the pulse input signals. It should be noted that the noise reduction achieved by sample/hold circuit 21 improves as the pulse rate increases since the delay between the sampling of the noise and the use of that noise to correct the signal decreases. It should also be noted that the LEDs do not have to be activated for the entire period of a timing pulse, but can be activated for only a portion of such a pulse. In this way, even higher currents can be applied to the LEDs for very short periods of time so as to achieve even higher intensity light bursts.

In practice, sensor 13 is applied to the patient's abdomen by, for example, applying medical tape to the back of head 15 or by including an adhesive layer as part of the head. Alternatively, sensor 13 can be incorporated in another monitoring system, such as, a fetal monitor, including fetal monitors using ultrasound. Sensor 13 can either be reusable or disposable after a single use. The patient can be an animal or a human.

Figure 6:
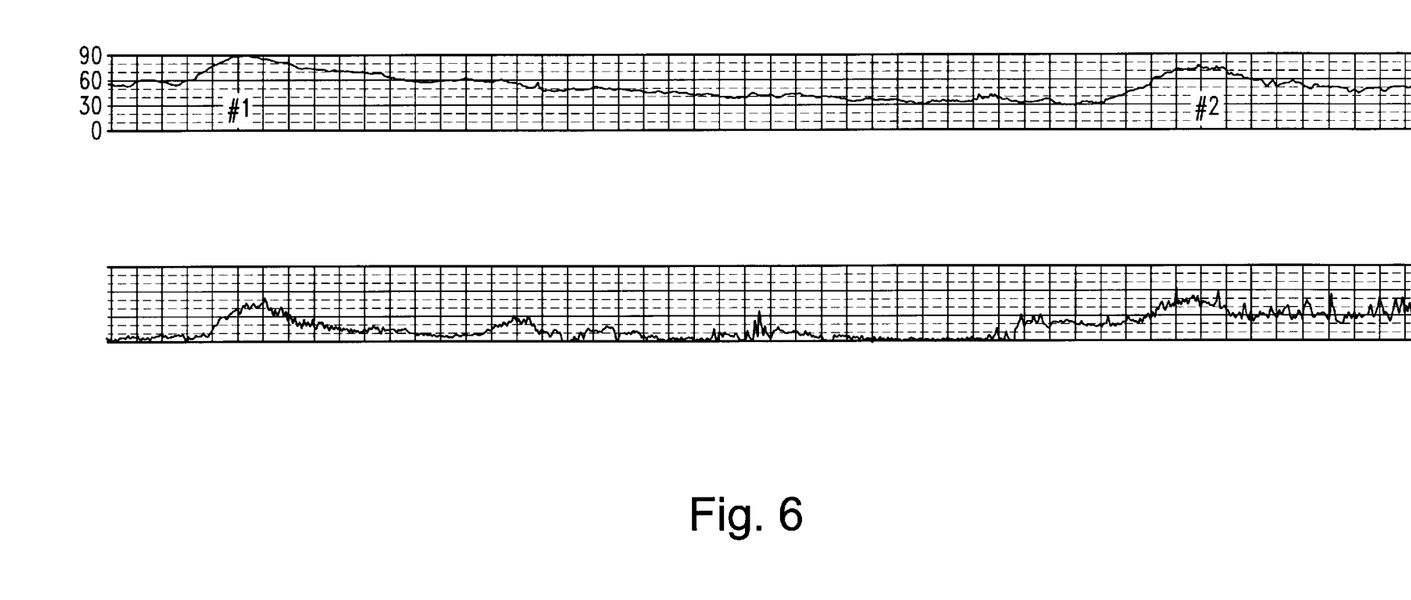
FIG. 6 shows a comparison of tracings obtained using a conventional tocodynamometer (bottom trace) and the system of the present invention (top trace). The horizontal axis in FIG. 6 represents time, with each division representing 20 seconds. The vertical axis represents relative output voltage.

FIG. 6 shows a comparison of tracings obtained using a conventional tocodynamometer (bottom trace) and the system of the present invention (top trace). The tracings were taken at the same time, with the sensor of the present invention and the tocodynamometer both being located in the patient's fundal area at substantially symmetric locations relative to the patient's center line.

The circuits, components, and drive currents of the '630 patent (see, in particular, FIGS. 1–4 of that patent) were used to obtain the trace of the invention shown in FIG. 6. In particular, the trace shown represents the difference in the outputs of elements 68 and 70 of FIG. 1B of the '630 patent. The relevant portions of the '630 patent are incorporated herein by reference.

FIG. 6 shows two contractions of the patient's uterus, both of which were detected by the system of the present invention and by the conventional tocodynamometer.

Figure 7:
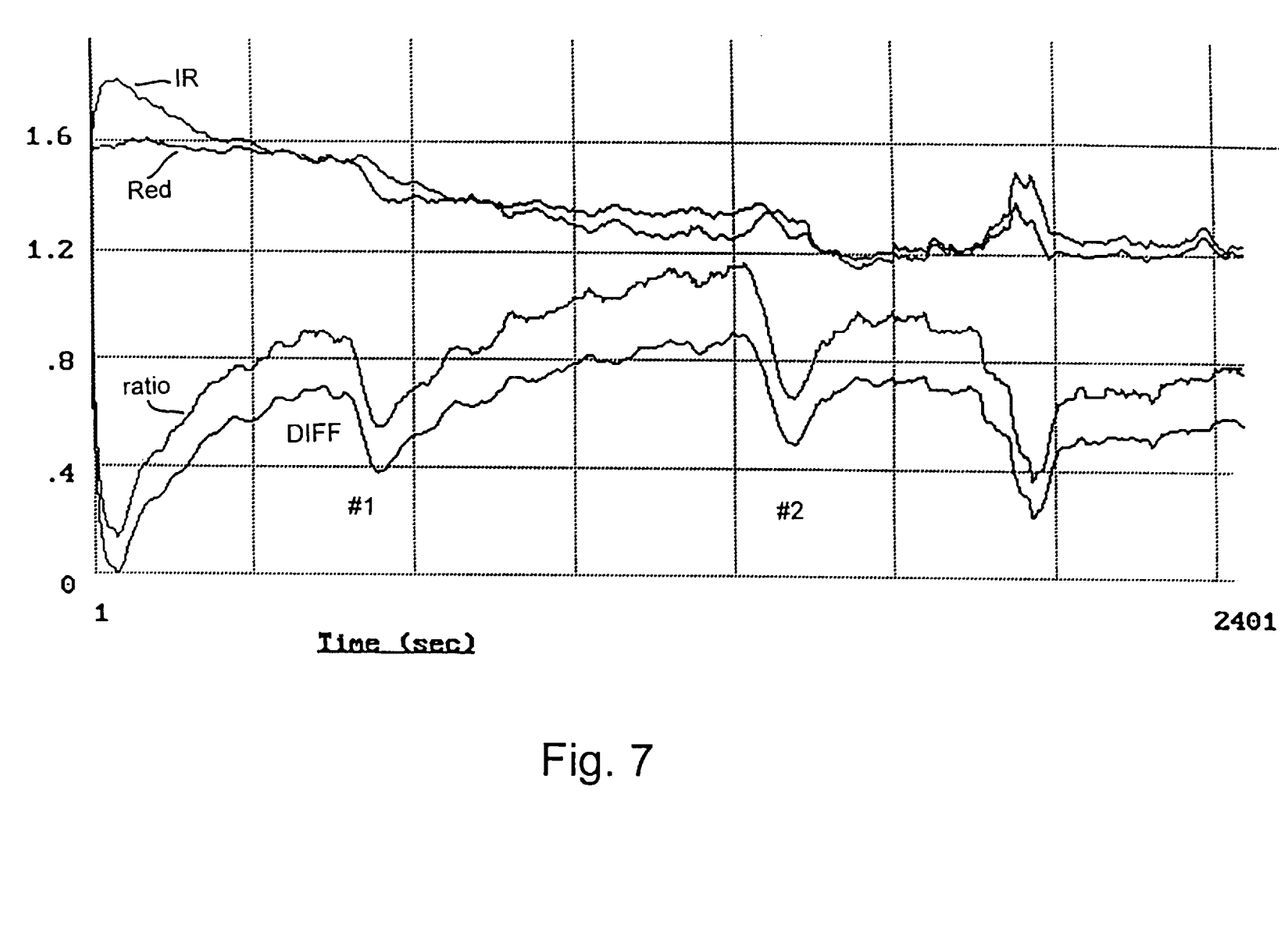
FIG. 7 shows IR and red light tracings obtained using the system of the present invention along with their ratio and difference. The horizontal axis represents time, with the full scale being about 40 minutes. The vertical axis represents relative voltage for the IR and red traces, and relative voltage times 10 for the difference and ratio traces.

FIG. 7 shows the data of the upper trace of FIG. 6 on a condensed time scale. It also shows the individual red (640 nm) and IR (940 nm) traces, as well as their ratio and difference (note that the upper trace of FIG. 6 is the difference between the red and IR traces). The first two distinctive dips in the ratio and difference curves of FIG. 7 correspond to the first and second uterine contractions of FIG. 6, while the third distinctive dip corresponds to a movement of the fetus in the region of the sensor.

Figure 8:
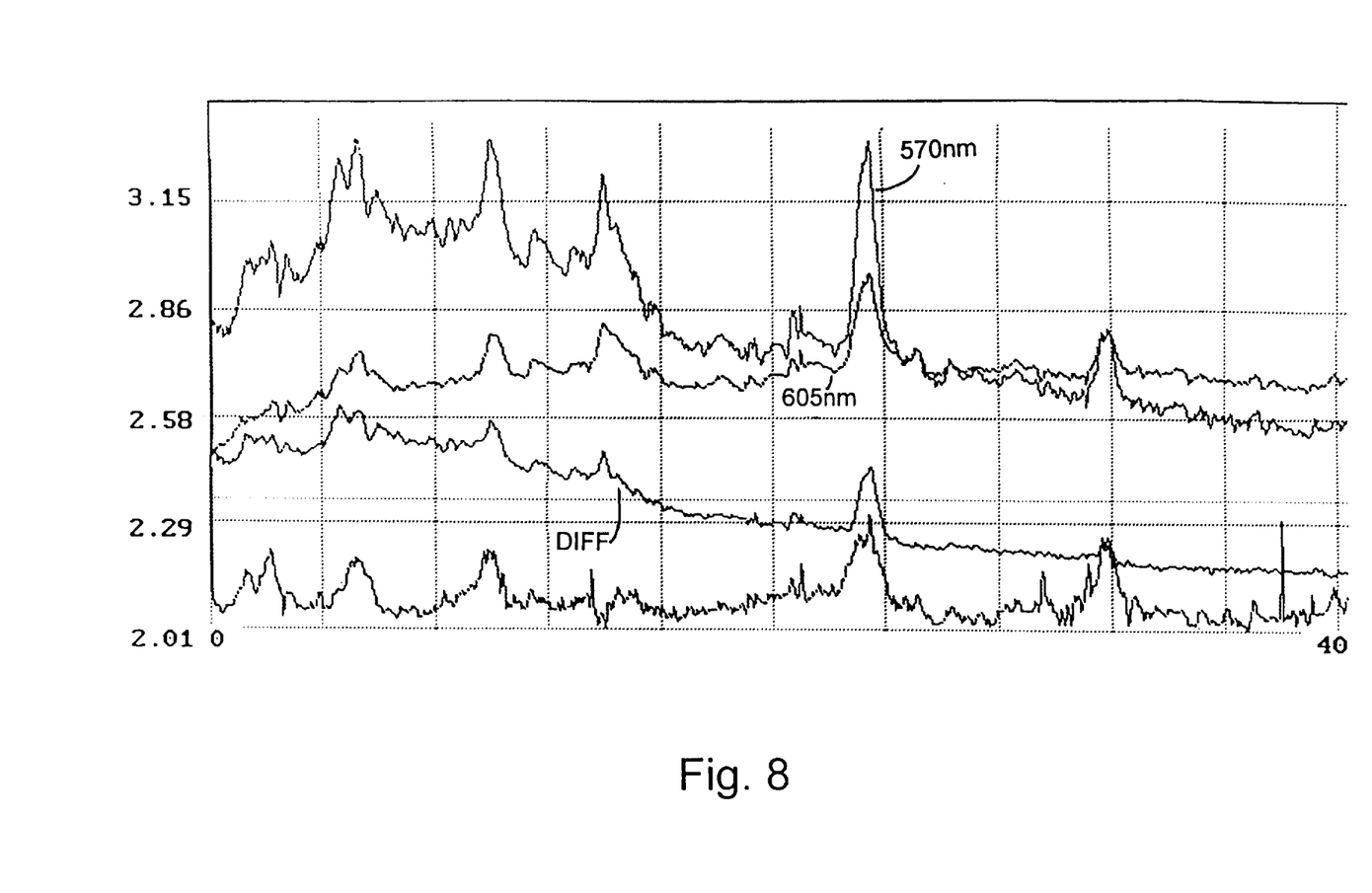
FIG. 8 shows tracings obtained using the system of the present invention (top two traces) along with their difference (third trace) and a tracing obtained with a conventional tocodynamometer (bottom trace). The wavelength used for the top trace was 570 nm and that for the second trace was 605 nm. The horizontal axis represents time, with the full scale being about 40 minutes. The vertical axis represents relative amplitudes with the raw data being multiplied by 2 for the top trace, by 1 for the second trace, and by −14 for the third trace. The amplitude of the bottom trace was adjusted for convenient presentation on the graph of this figure.

FIG. 8 shows curves obtained using the circuit and timing diagram of FIGS. 4 and 5 with light sources of 570 nm and 605 nm. The upper curve in this figure shows the 570 nm trace, the second curve shows the 605 nm trace, the third curve shows the difference between the first and second curves, and the bottom curve shows a tracing obtained at the same time from a conventional tocodynamometer. As shown in this figure, the technique of the invention again is comparable to a conventional tocodynamometer in its ability to monitor uterine contractions.

Although specific embodiments of the invention have been described and illustrated, it is to be understood that modifications can be made without departing from the invention's spirit and scope. For example, although the experimental data presented above was obtained using two wavelengths of light, either more or less wavelengths can be used if desired. In particular, uterine activity can be monitored using a single wavelength, which, as discussed above, is preferably in the red/orange region of the spectrum. More than two wavelengths can be used, for example, to stabilize the baseline of the trace produced by the monitor.

Because of their small size, the sensors of the invention can be used to monitor the spatial and/or temporal course of a uterine contraction. Specifically, a plurality of sensors, i.e., an array of sensors, can be placed on the patient's abdomen at different locations and used to analyze the spatial form and/or temporal sequence of the contractive wave along the patient's abdomen. Such distributed monitoring was used in experimental settings in the past (see Reynolds, *Physiology of the Uterus,* Paul B. Hoeber, Inc., New York, 1949, pages 42–53), but has not been adopted in clinical practice due to, among other things, the relatively large size of mechanical transducers in comparison to the limited surface area of the abdomen.

At least three sensors are preferably used in distributed monitoring to detect activity in the fundus, in the mid portion of the uterus, and in the lower uterine segment. More or less locations can, of course, be used. Also, multiple sensors can be used to monitor each portion of the uterus. The apparatus and procedures described above for the single sensor embodiments can be used with the multiple sensor embodiments with appropriate changes being made to the monitor to accommodate the additional sensors, which changes will be evident to persons skilled in the art from the disclosure herein.

A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A method for monitoring uterine activity of a gravid patient comprising:

applying light to the patient's abdominal wall so that the light passes into the tissues of the patient's abdominal wall and is then detectable at an external surface of the abdominal wall, the magnitude of the light that is detectable being a function of the volume of blood in the abdominal wall;

detecting the light at the external surface of the abdominal wall;

transforming the detected light into an electrical signal that is indicative of the volume of blood in the abdominal wall; and monitoring the electrical signal to detect uterine activity.

2. The method of claim 1 wherein the light has a wavelength in a range where the absorptions of at least some hemoglobin fractions of blood are similar.

3. The method of claim 2 wherein the light has a wavelength in a range where the absorptions of the major hemoglobin fractions are similar.

4. The method of claim 3 wherein the light has a wavelength in a range where the absorptions of oxyhemoglobin and deoxyhemoglobin are similar.

5. The method of claim 4 wherein the light has a wavelength in the range from about 500 nm to about 600 nm.

6. The method of claim 4 wherein the light has a wavelength of about 800 nm.

7. A method for monitoring uterine activity of a gravid patient comprising:

applying light of a first wavelength to the patient's abdominal wall so that the light passes into the tissues of the patient's abdominal wall, the first wavelength being selected so that the absorption of light of the first wavelength passing into the abdominal wall is substantially insensitive to the level of oxygen saturation of blood in the tissues;

detecting the light of the first wavelength which has passed into the tissues of the abdominal wall and is detectable at an external surface of the abdominal wall;

transforming the detected light of the first wavelength into a first electrical signal;

applying light of a second wavelength to the patient's abdominal wall so that the light passes into the tissues of the patient's abdominal wall, the second wavelength being selected so that the absorption of light of the second wavelength passing into the abdominal wall is substantially insensitive to the level of oxygen saturation of blood in the tissues;

detecting the light of the second wavelength which has passed into the tissues of the abdominal wall and is detectable at an external surface of the abdominal wall;

transforming the detected light of the second wavelength into a second electrical signal;

processing the first and second electrical signals to form a third electrical signal; and monitoring the third electrical signal to detect uterine activity.

8. The method of claim 7 wherein the light having the first wavelength is absorbed by blood to a different extent than the light having the second wavelength.

9. The method of claim 7 wherein the step of processing the first and second electrical signals to form a third electrical signal comprises determining the difference between the first and second electrical signals.

10. The method of claim 7 wherein the step of processing the first and second electrical signals to form a third electrical signal comprises determining the ratio of the first and second electrical signals.

11. A method for monitoring uterine activity of a gravid patient comprising:

applying light of at least one wavelength to at least two locations on the patient's abdominal wall, so that the light passes into the tissues of the patient's abdominal wall at each of the locations, the wavelengths being selected so that the absorption of light of the wavelengths passing into the abdominal wall is substantially insensitive to the level of oxygen saturation of blood in the tissues;

detecting the light which has passed into the tissues of the abdominal wall and is detectable at an external surface of the abdominal wall at each of the locations;

for each of the locations, transforming the detected light into an electrical signal that is indicative of the volume of blood in the abdominal wall, one signal for each location; and monitoring the electrical signals produced in the step of transforming the detected light into an electrical signal to detect uterine activity.

\* \* \* \* \*